United States Patent [19]

Wu et al.

[11] Patent Number: 5,099,012
[45] Date of Patent: Mar. 24, 1992

[54] CHROMAN-2-CARBOXAMIDE CONJUGATES AND THEIR USE FOR TREATMENT OF REPERFUSION INJURY

[75] Inventors: Tai-Wing Wu; Donald A. G. Mickle, both of Toronto, Canada

[73] Assignee: Eastman Kodak Company, Rochester, N.Y.

[21] Appl. No.: 626,116

[22] Filed: Dec. 11, 1990

[51] Int. Cl.⁵ .............................................. A61K 31/35
[52] U.S. Cl. .................................. 536/17.5; 514/456; 514/458; 514/474; 514/824; 514/25
[58] Field of Search .................. 514/824, 456, 458, 25, 514/474; 536/17.5

[56] References Cited

U.S. PATENT DOCUMENTS 4,401,661 8/1983 Schaub et al. ...................... 424/180
4,877,810 10/1989 Mickle et al. ........................ 514/456

OTHER PUBLICATIONS

Mickle et al. *Ann. Thorac. Surg. 47,* 553–557 (1989), "Myocardial Salvage with Trolox and Ascorbic Acid for an Acute Evolving Infarction".
Taylor et al., *J. Am. Oil Chem. Soc. 58,* 622–626 (1981), "Antioxidant Activity of Amino Acids Bound to Trolox-C ®".
Schacht et al., *J. Controlled Release 1,* 33–46 (1984), "Polymer-Drug Combinations: Synthesis and Characterization of Modified Polysaccharides Containing Procainamide Moieties".
Molteni, *Methods in Enzymology 112,* 285–298 (1985), "Dextran and Inulin Conjugates as Drug Carriers".
Arnold, *Methods in Enzymology 112,* 270–285 (1985), "Polylysine-Drug Conjugates".

*Primary Examiner*—Ronald W. Griffin
*Attorney, Agent, or Firm*—Philip E. Hansen; Paul E. Dupont

[57] ABSTRACT

Conjugates of 6-hydroxy-2,5,7,8-tetramethylchroman-2-carboxylic acid with p-aminophenylsaccharides, with aminoalkyl-derivatized dextrans and with polylysines and polyornithines are prepared by condensation using diimides. Methods and compositions for the use of such conjugates to protect mammals from reperfusion injury are also disclosed.

28 Claims, No Drawings

CHROMAN-2-CARBOXAMIDE CONJUGATES AND THEIR USE FOR TREATMENT OF REPERFUSION INJURY

BACKGROUND OF THE INVENTION

1. Field of the Invention

The present invention relates to novel amide conjugates of 6-hydroxy-2,5,7,8-tetramethylchroman-2-carboxylic acid with derivatized monosaccharides, oligosaccharides, polysaccharides and with polylysine and polyornithine. The invention also relates to compositions containing these conjugates and the use of the conjugates for the prevention and treatment of reperfusion injury.

2. Information Disclosure Statement

U.S Pat. No. 4,877,810 to Mickle and Wu discloses the use of 6-hydroxy-2,5,7,8-tetramethylchroman-2-carboxylic acid (also known as Trolox-C and hereinafter sometimes referred to as TX) for the treatment of cardiac reperfusion injury. Mickle et al. [*Ann. Thor. Surg.* 553-557 (1989)] also discloses the use of TX for the treatment of reperfusion injury in cardiac tissue.

Taylor et. al [*Journal of the American Oil Chemical Society,* 622-626 (1981)] describe amides of TX with naturally occurring α-aminoacids. Specifically disclosed are TX-methionine, TX-tryptophan, TX-histidine and TX-cysteine. The antioxidant activity of the compounds is described in linoleate emulsions and in edible oils such as corn oil.

Schachtet. al. [*J. Controlled Release* 1, 33-46 (1984)] describe the oxidation of dextran (molecular weight 43,000) with periodate, the condensation of the resulting polyaldehyde with N-(ω- aminoalkanoyl)-procainamides and the reduction of the condensation products with sodium cyanoborohydride to provide conjugates of dextran linked to procainamide. The general chemistry of dextran as a drug carrier has been reviewed by Molteni [*Methods in Enzymology* 112, 285-298 (1985)].

Arnold [*Methods in Enzymology* 112, 270-285 (1985)] describes conjugates of antineoplastic agents with polylysine. Specifically disclosed are conjugates of methotrexate, anthracyclin and 6-aminonicotinamide with polylysine of $\overline{M}w$ 13000, 35000, and 70000.

U.S. Pat. No. 4,401,661 to Schaub et al. discloses N,N'-bis[4-[4-O -(α-D-glucopyranosyl)-β-D-glucopyranosyloxy]-phenyl]butanediamide as an intermediate in the synthesis of sulfonated diamine complement modulators.

SUMMARY OF THE INVENTION

In a product aspect, the invention relates to compounds of the formula I

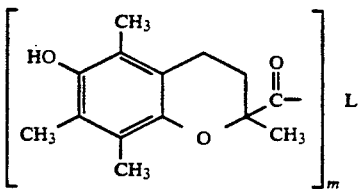

wherein m is an integer from 1 to 10 and L is chosen from the group consisting of:

(1)

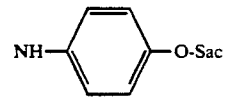

wherein Sac is a mono-, di- or trisaccharide, preferably a disaccharide, more preferably cellobiose, maltose or gentiobiose, most preferably lactose;

(2)

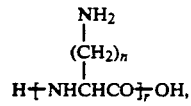

or a pharmaceutically acceptable cationic or anionic salt thereof, wherein n is three (polyornithine) or four (polylysine), r is an integer from 3 to 200, preferably from 140 to 160, and the chroman is attached to L by the replacement of a hydrogen on a side chain nitrogen; and (3) [—NH(CH$_2$)$_p$NH—]$_q$—D wherein p is an integer from 2 to 12, preferably 6, D is a functionalized dextran of molecular weight from 1250 to 30000, preferably from 1250 to 10000, most preferably about 9400, and q is an integer from 1 to 12, L the value of which is not less than m and is in the range from $1 \times 10^{-4}$ to $7 \times 10^{-4}$ times the average molecular weight of D.

It will be apparent that in the case where L is

m must be 1. In the case where L is polylysine or polyornithine, it is preferred that m be 2 or greater and most preferably 2, 3 or 4. In the case where L is [—NH(CH$_2$)$_p$NH—]$_q$—D for dextran of $\overline{m}w$ from 1250 to 10000, the preferred range of m is from 1 to 5 and the preferred range of q is from 1 to 6. For dextran of $\overline{M}w=9400$ the preferred range of m is from 4 to 5 and the preferred range of q is from 4 to 6.

A precise structural representation of the preferred embodiment of the dextran conjugate being difficult to depict, this aspect of the invention may be further characterized as the product of a process which comprises the steps of:

(1) oxidizing dextran of average molecular weight 9400 with about 0.5 equivalents of sodium periodate;

(2) condensing the oxidized dextran at a concentration of 0.5% in aqueous buffer with about 10 equivalents of 1,6-hexanediamine at pH 7.2;

(3) reducing the dextran-hexanediamine Schiff base with about 10 equivalents of sodium borohydride at pH 9.0; and (4) coupling the aminohexylaminodextran with about 1 equivalent of 6-hydroxy-2,5,7,8-tetramethylchroman-2-carboxylic acid in the presence of 2 equivalents of 1-(3-dimethylamino)-3-ethylcarbodiimide at pH 5.5 to 6.5.

In a method aspect, the invention relates to a method of using the conjugates of the invention for the protection of cells from the injury that is associated with reperfusion following ischemia.

In a further method aspect, the invention relates to a method of using the conjugates of the invention for protecting a mammal from tissue injury that is associated with reperfusion following ischemia.

In a composition aspect, the invention relates to pharmaceutical compositions containing the conjugates of the invention.

DETAILED DESCRIPTION INCLUSIVE OF PREFERRED EMBODIMENTS

The compounds of the invention may be prepared by condensation of 6hydroxy-2,5,7,8-tetramethylchroman-2-carboxylic acid (TX) with the appropriate amine. Many methods for the formation of amides from acids and amines are known in the art, among which the use of carbodiimides is particularly recommended for compounds of formula I:

mined for any condensation product by the Folin-Wu reaction [Lowry et al. *J. Biol Chem.* 193, 265-275 (1951)]. TX as a potent antioxidant reduces this reagent. To 0.5 mL of sample in water is added 2.5 mL of 2% $Na_2CO_3$ in 0.1N NaOH followed by 0.25 mL of 1 N Folin-Wu reagent. The absorption of this solution at 750 nm is read after 15 min in a spectrophotometer. The concentration of the TX in TX conjugates is determined from a standard curve constructed using a series of concentrations of authentic TX between 0 and 1 mM.

The reaction of about 1 equivalent of TX with 0.6 equivalents of polylysine of e,ovs/M/ w=20000 (n=4; r=156) and 1 equivalent of carbodiimide for about 17 hours at ambient temperature provides about two TX residues per polymer. The same reaction conditions with polylysine of $\overline{M}w=9000$ (n=4; r=70) provides between 3 and 4 residues of TX per polymer. We have found that when the average of the values of m is less than 2.0, the polymers are of significantly lower solubil-

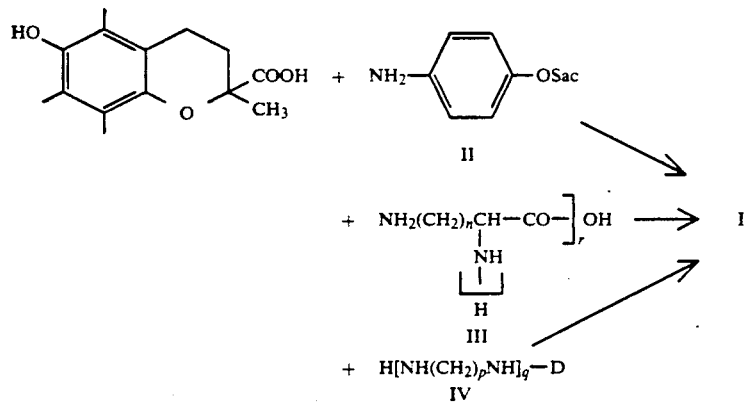

Trolox in aqueous solution at pH 6.0 is treated with about 0.5 equivalents of II in the presence of 2 equivalents of suitable water-soluble carbodiimide, preferably 1-ethyl-3-(3-dimethylaminopropyl)carbodiimide (EDC) or about 0.6 equivalents of III in the presence of 1 equivalent of a water-soluble carbodiimide, preferably EDC, or about 2 equivalents of IV (based on primary amino functions) in the presence of 2 equivalents of a water-soluble carbodiimide, preferably EDC.

The starting materials II are well known in the art. Many of the aminophenylmonosaccharides and some of the aminophenyldisaccharides are commercially available. Those that are not commercially available may be synthesized according to the method of Babers and Goebel [*J. Biol. Chem.* 105, 473 (1934)] from the mono-, di- or trisaccharide by peracetylation, displacement of the anomeric acetate by HBr, displacement of the bromine by p-nitrophenol, and reduction of the nitrophenol. It will be apparent to those skilled in the art that this method is applicable only to reducing saccharides, and saccharide in the context of the present invention refers to reducing saccharides.

The starting materials III are readily available. Many polylysines and polyornithines of varying $\overline{M}w$ are commercially available, and the synthesis of polylysines and polyornithines is well known in the art. The coupling of TX with varying numbers of side-chain amino functions in the polymers may be controlled primarily by the ratio of TX to polymer and secondarily by the duration of the coupling reaction. The ratio of TX to polymer (i.e. the average of the values of m in formula I) may be deterity in water.

The starting materials IV are likewise readily available by syntheses well known in the art. Dextran of appropriate e,ovs/M/ w is oxidized with periodate, condensed with the appropriate diamine and reduced with borohydride according to a procedure analogous to that described by Schacht et al. [*J. Controlled Release* 1, 33-46 (1984)]. The precise structure of the oxidized dextran has not been established, but the literature indicates that it is a mixture of dialdehydes arising from the cleavage of the vicinal diols of the individual glucose subunits. The number and location of dialdehydes in the polymer is not known but a % oxidation is calculated by the number of mmols of periodate consumed in the reaction. We have found that biologically active conjugates can be made when the % oxidation is about 50%. This is achieved by oxidizing 1 equivalent of dextran (based on glucose residues) with 0.5 equivalents of sodium periodate at ambient temperature for 12 hours.

The "dialdehyde dextran" is condensed immediately with about 8 to 10 equivalents of an alkanediamine, preferably 1,6-hexanediamine, at pH 7.0 to 7.4 and then reduced at about pH 9.0 with about 10 equivalents of sodium borohydride. The condensation reaction should be done at relatively high dilution (less than 1%) to minimize cross-linking of aldehydes. We have found 0.5% aqueous solutions to be particularly suitable. Sodium borohydride could be replaced by sodium cyanoborohydride in the reduction of the imine to the amine, in which case the pH is appropriately lowered to pH 4 to 6.

The compounds of the invention may be incorporated in pharmaceutical compositions. Any pharmaceutically acceptable oral vehicle compatible with the compounds of the invention may be used for oral administration, such as water, aqueous alcohol, oil or oil-water emulsions. In addition one may prepare unit dosage forms incorporating excipients, binders, glidants, etc. for tablets or capsules. In a preferred embodiment, the compounds of the invention are incorporated in parenteral compositions which may be administered directly into the bloodstream, or intramuscularly or intraperitoneally. For parenteral compositions, physiological saline, dextrose, Ringer's lactate or other commonly used intravenous vehicles may be used. When the compounds are to be used ex vivo, as for example in organ transplantation, other cardioplegic or organ-preserving vehicles may be used as well.

EXAMPLES

Example 1

Lactosylphenyl-trolox. To 5 mL of a solution containing 216 mg (0.5 mmols) of p-aminophenyl-$\beta$-D-lactopyranoside dissolved in deionized, nitrogen-purged water and adjusted to pH 6.0 was added 250 mg (1 mmol) of TX, followed by 400 mg of EDC (2 mmol). The reaction mixture was stirred for 16 h at room temperature. Deionized water was added to the reaction mixture to a final volume of 10 mL. The latter was mixed thoroughly with 40 mL of chloroform-methanol (2:1) and allowed to stand for 10-15 min. Two clear phases were formed. The upper phase was removed by aspiration and the lower phase was washed 4 times with chloroform/methanol/water (3:48:47). The washed lower phase was concentrated under a gentle stream of nitrogen and analyzed by thin layer chromatography (TLC) on silica gel plate with fluorescent indicator. The plate was developed in chloroform/methanol/water (60:35:8). After chromatography, the dried plate was viewed under short-wavelength UV light for the presence of chroman and subsequently sprayed with orcinol reagent for the detection of carbohydrates. There was one band (RF=0.60) that was both UV-absorbing and orcinolpositive. A product corresponding to this band or material was further purified on a preparative TLC plate of the same type as that above but developed with chloroform/methanol/water (60:35:8). The lactosylphenyl-trolox, which appeared as a strong UV-absorbing band was scraped off the plate and extracted with chloroform/methanol (2:1).

Example 2

Galactosylphenyl-trolox. By a process analogous to that of Example 1, galactosylphenyl-trolox was prepared from p-aminophenyl-$\beta$-D-galactopyranoside and trolox.

Example 3

Kojibiosylphenyl-trolox. By a process analogous to that of Example 1, it is contemplated that kojibiosylphenyl-trolox may be synthesized from TX and 4-aminophenyl-2-O-$\alpha$-D-glucopyranosyl-D-glcoside (p-aminophenylkojibioside), which may be prepared according to Duke et al. [*Carbohydrate Res.* 27, 193-198 (1973)].

Example 4

Xylosylphenyl-trolox. By a process analogous to that of Example 1, it is contemplated that xylosylphenyl-trolox may be synthesized from TX and p-aminophenyl-$\beta$-D-xylopyranoside.

Example 5

Cellotriosylphenyl-trolox. By a process analogous to that of Example 1, it is contemplated that cellotriosylphenyl-trolox may be synthesized from TX and p-aminophenylcellotrioside. It is further contemplated that the p-aminophenylcellotrioside may be synthesized from cellotriose hendecaaacetate by the procedure of Babers and Goebel described above.

Example 6

Dextran-trolox. Five hundred mg of dextran (average molecular weight 9,400 daltons) containing 3 mmols of glucose residue, were dissolved in 50 mL of 0.03M (1.5 mmol) of sodium periodate and kept at room temperature for 12 h in the dark. The reaction mixture was dialyzed against deionized water in darkness and freeze-dried. The concentrations of reagents were selected to obtain approximately 50% oxidation of the dextran. The resulting polyaldehyde-dextran (PAD) was used immediately in the next step. PAD (equivalent of 1.2 mmol) of aldehyde functions) was dissolved in 100 mL of 0.1M sodium phosphate buffer, pH 7.2, and to this 1.1 g (10 mmols) of 1,6-hexanediamine was added with stirring. The pH of the mixture was adjusted to 9.0, followed by addition of 0.38 g of sodium borohydride. The reaction was carried out at room temperature in the dark for 16 h. The reaction mixture was dialyzed against deionized water and lyophilized. The presence of free amino groups (aliphatic) was demonstrated by color reaction with picrosulfonic acid. Two hundred mg of aminated PAD from Step 2 were dissolved in 20 mL of deionized, nitrogen-purged water, which was adjusted to pH 6.0 by 0.3N HCl. To this 125 mg (0.5 mmols) of TX were added, followed by 200 mg (1 mmol) of EDC. With the pH maintained between 5.5 and 6.5, the reaction mixture was stirred for 16 h at room temperature, before being dialyzed against deionized water and lyophilized. The ratio of TX to dextran in Dex-TX was estimated to average 4.2 by the Folin-Wu reagent as described earlier.

It is contemplated that dextran-trolox conjugates having different linkers (i.e. p in formula I is other than 6) may be synthesized by the foregoing procedure, substituting the appropriate diamine for 1,6 hexanediamine.

Example 7

Polylysyl 19,000)-trolox. Two hundred mg of polylysine-HBr (MW=19,000) (equivalent to 1.6 mmols of lysine) was dissolved in 6 mL of deionized water pre-purged with nitrogen and adjusted with 0.2N NaOH to pH 6.0. To this was added 250 mg (1 mmol) of Tx, followed by 200 mg (1 mmol) of EDC. With the pH maintained at or near 6.0, the reaction mixture was stirred for 17 h at room temperature and preferably under a stream of nitrogen. The reaction mixture was dialyzed against deionized water and lyophilized. The ratio of TX to polylysine in the resultant product was estimated to be 2.3 based on its reaction with the Folin-Wu reagent.

Example 8

Polylysyl (9000)-trolox. By a procedure analogous to that of Example 7, polylysyl (9000)-trolox was synthesized from polylysine ($\overline{M}w=8858$) and TX. It was determined that there were an average of 3.7 TX residues per polylysine.

It is contemplated that polyornithyl-troloxes of varying e,ovs/M/ w may be synthesized by a procedure analogous to that of Example 6 substituting the appropriate polyornithine for polylysine. The compounds of this invention display protective and restorative activity against reperfusion injury as shown by the results of standard tests carried out on representative examples as described below.

Assay 1: Myocyte-based Assay

A hypoxanthine-xanthine oxidase system as described by Wu et al. [Biochem. & Cell Biol. 68, 1189-1194 (1990)] was used to generate free radicals in situ. The extent of damage inflicted by the free radicals on cultured human ventricular myocytes in the absence (control) or presence of a presumptive antioxidant serves to assess the relative efficacies of the different derivatives tested. Early damage was signaled by such morphological changes as cell shrinkage and appearance of a "halo" in the periphery of the myocyte. Cell viability was gauged by conventional techniques such as trypan blue exclusion and $Cr^{51}$ leakage. The correlation of cell death with these markers was confirmed by electron microscopy at 17,000X. The time taken to attain definitive necrosis in $10^5$ cells per mM of compound tested was taken as the index of comparison of results.

Biopsied heart muscle from non-cardiac patients was the source of myocytes used for cell culture. Eighty to 400 mg of fresh tissue was incubated with 5-10 mL of an enzyme solution containing 0.1% collagenase, 0.2% trypsin in $Ca^{2+}$- and $Mg^{2+}$-free phosphate buffered saline, pH 7.3, at 37° C. with gentle shaking. After 15-20 min, the incubation mixture was decanted into a vial containing an equal volume of DMEM culture medium containing 10% fetal bovine serum and penicillin-streptomycin. Undigested tissue was treated as above and all incubation mixtures were collected and centrifuged at 5,000 Xg for 15 min. After the supernatant fluid was discarded, the cells were suspended in fresh medium and counted in a hemocytometer. Then the cells were incubated at 37° C. under 5% $CO_2$ at a concentration of $6-8\times10^5$. Following incubation for 1 h, the supernatant fluid was transferred to another culture dish. After 2-3 days, D-arabinofuranosylcytosine (ara-C) was added to the medium to reach a final concentration of 10 μM and incubated for 24-48 h. Then the medium was replaced by one without ara-C. When the cells reached confluence, they were separated by trypsin treatment. The cells were ready for experiments by 7-10 days after separation.

In the actual experiment, approximately $2\times10^5$ cultured human myocytes in 6 mL of phosphate-buffered saline, pH 7.4, were incubated with the compounds of the examples (over a range of concentrations) for 5 min before addition of 16 IU/L of xanthine oxidase and 1 mM of hypoxanthine to induce free radical injury on the cells. In controls, myocytes incubated alone or with either xanthine oxidase or hypoxanthine exhibited no discernible change in morphology or viability for at least 45 min. The results are presented in Table I.

TABLE I

Damage of Cultured Human Myocytes by Free Radicals in the Absence or Presence of TX and Compounds of the Examples

| | Actual Time Required for Damage of $10^5$ Cells (min/mM tested compound) | Delay in Time[a] |
|---|---|---|
| Cells (+ free radicals) | 1.9 | 0 |
| TX (0-1.34 mM)[b] | 5.1 | 3.2 |
| Example 1 (0.1-0.8 mM) | 14.0 | 12.1 |
| Example 7 (0.28-0.84 mM) | 6.7 | 4.8 |
| Example 6 (0.5-1.0 mM) | 4.7 | 2.8 |
| Polylysine (0-2.0 mM) | 2.3 | 0.4 |
| Dextran (0.1-1.0 mM) | 0.0 | — |
| p-Aminophenyllactoside (0-1.0 mM) | 2.0 | 0.1 |

[a] For each tested compound, the result was averaged from 2-5 closely agreeing replicates per condition.
[b] Numbers within brackets indicate range of concentrations tested over which the effect was roughly proportional to level of compound tested, and from which the data for 1.0 mM was derived.

Assay 2: Human Erythrocyte (RBC) System

In this system, human RBC in suspension were exposed to free radicals generated by thermal decomposition of 2,2'-azo-bis-(2-amidinopropane) HCl (AAPH). This resulted in lysis of the red cells. The extent of hemolysis was quantitatively determined by measuring the amount of hemoglobin (based on its absorption at 541 mm) in the supernatant fluid after the cell debris plus unlysec RBC were spun down. The efficacy of the compounds of the examples in scavenging free radicals and hence in preventing hemolysis was expressed as that concentration of the compound required to inhibit 50% of cell lysis under defined experimental conditions. Each presumptive antioxidant examined was tested in a minimum of triplicates and at multiple concentrations.

In the actual experiment, human blood samples were collected from healthy donors into 6 mL Vacutainer tubes containing EDTA. The plasma and buffy coats were separated from RBC by centrifugation at $1,000\times g$ for 10 min. The RBC were washed 3 times with saline and the packed erythrocytes were suspended in 4 volumes of 10 mM phosphate-buffered saline, pH 7.4 to give a 20% suspension. The latter was mixed with an equal volume of compound to be tested in 10 mM phosphate-buffered saline solution to which was added AAPH to a final concentration of 100 mM. The reaction mixture was shaken gently in a water bath set at 37° C. for 3 h. Then aliquots of the incubated mixture were diluted 40 times with either saline or water. Saline-diluted samples were centrifuged at $1,000\times g$ for 10 min and the absorbance (A) of the supernatant fluid was measured at 541 nm. Samples diluted with water were spun down at $13,000\times g$ for 10 min and the $A_{541}$ nm of the supernatant fluid was taken as the reference for 100% hemolysis (B). Inhibition of hemolysis was calculated from the formula: $[1-(A/B)]\times100$=percent (%) inhibition of hemolysis. The latter was plotted against concentration of the TX content in TX or its synthetic conjugate. From the plot, the level of the compound that gave 50% inhibition of hemolysis was determined. At each level of the compound tested, the average of 3 or more closely agreeing replicates is reported in Table II.

TABLE II

| Reduction of Free Radical-Induced Lysis of Human Red Cells by TX and Compounds of the Examples | |
|---|---|
| Compound | IC$_{50}$, or that concentration of antioxidant which reduces red cell lysis by 50% (mM) |
| TX | 0.34 |
| Ascorbate | 1.07 |
| L-cysteine | >1 |
| Example 1 | 0.16 |
| Example 6 | Not Determined[a] |
| Example 7 | Not Determined[a] |

[a]Not determined because these conjugates, and the polymers dextran and polylysine alone, affect the sedimentation properties of erythrocytes.

Assay 3: Rat Hepatocyte System

A dose response curve in isolated rat hepatocytes was generated as follows:

Hepatocytes were obtained from male Sprague-Dawley rats by the method of P. O. Seglen [*Exp. Cell Res.* 82, 391–398 (1973)]. Studies were performed by plating the cells and adding 3 mL of phosphate-buffered saline (pH 7.4, 37° C.) containing xanthine oxidase (66.7 IU/L) and hypoxanthine (2 mM). The addition of hypoxanthine alone did not produce any morphological changes by 1 hour. The compound of Example 2 was added 1 minute before the addition of the free-radical generating system. Cell necrosis was determined by nuclear shrinkage, membrane rupture or a halo-like appearance around the cells. Table III shows the time in minutes to necrose $10^5$ cells.

TABLE III

| Concentration of 2 (mM) | Time to Necrose $10^5$ Hepatocytes |
|---|---|
| 0 (control) | 8.6 |
| 0.2 | 12.2 |
| 0.4 | 14.7 |
| 0.8 | 15.5 |
| 1.2 | 19.5 |
| 1.6 | 19.1 |

Assay 4 Rat Liver Ischemia Reperfusion in Vivo

Two groups of 6 each of male Sprague Dawley rats weighing between 300 and 600 g were used. Immediately before surgery, the animals were given 10 mg gentamicin intramuscularly, anesthetized with an ethrane inhalant, and injected intraperitoneally with heparin (100 U/kg). Next the hepatic artery and portal vein were occluded for 70 minutes using pediatric Satinsky vascular clamps. Beginning 45 seconds prior to release of the occlusion, a 3 mL bolus of 1 mM solution of the compound of Example 1 (corresponding to 3 μmoles of compound or a dose of 7.5 to 10 mmoles/kg of body weight) or a control solution (the normal saline vehicle) were infused for the initial two minutes of reperfusion through the right renal vein using a butterfly needle. The animal was then given a 4 mL bolus of 3.75% sodium bicarbonate via the penile vein. At the end of 48 hours, the animal was anesthetized and sacrificed by exsanguination. The liver was harvested and placed in saline at room temperature prior to histological analysis. The results, which are statistically significant at the p<0.001 level, show 5.7±2.1% necrosis for the rats treated with the compound of Example 1 and 24.4±11.0% necrosis for the control rats; this corresponds to 77% organ salvage.

Assay 5: Rabbit Heart Model

New Zealand white rabbits (3–3.5 kg by weight) were anesthetized with an intramuscular injection of Ketamine (35 mg/kg) and Atravet (0.4 mg;kg) and an intravenous injection of atropine (0.1 mg/kg). Anesthesia was maintained by performing tracheotomy and ventilating the animal with positive pressure respiration using a Harvard small animal respirator and a gas mixture of 2.5% ethrane (or enflurane) in oxygen. A midline sternotomy was done. The pericardium was opened and the heart was exposed. The left circumflex coronary artery was temporarily ligated with a 5-0 silk thread for 1 hr at a site approximately midway from the apex to the atrio-ventricular groove. One minute before releasing the occlusion, a 30-mL bolus of a 1 mM solution of the compound of Example 1 was injected through the right external jugular vein. In control animals, a 30-mL bolus of normal saline was given instead of the test solution. In all cases, a 3-hr reperfusion followed. After this period, the heart was harvested, stained for enzyme activity with a tetrazolium dye and the areas of necrosis determined by planimetry.

To determine the area at risk, the original ligature in the heart was tightened, and an 22G angiocath was inserted into the aorta for injection of a 30-mL bolus of Evans' Blue solution. The heart was then sliced transversely into 2 mm thick slices and stained with 1.25% nitro red tetrazolium for 30 min. The negative nitro red tetrazolium staining pattern on each slice was traced on a transparent acetate sheet for calculating the necrotic area by computerized planimetry.

In this model, control saline infusion before reperfusion resulted in an average of 46.6±10% necrosis (n=7 rabbits). Infusion of 5.7 mg/kg of the compound of Example 1 (corresponding to 7.5 to 10 μmoles of compound) resulted in an average of 10.6±7.8% necrosis (n=7 rabbits). This indicates about 77% salvage.

The percentage of active component in the composition and method for treating or preventing reperfusion injury can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus be determined by the clinician considering all criteria and utilizing his best judgement on the patient's behalf. From studies with mammals it appears that doses between 1 and 100 μmoles per kg are effective.

We claim:

1. A compound of formula I

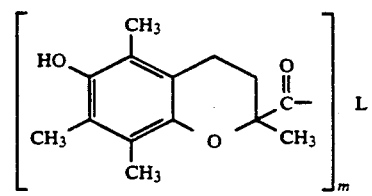

wherein m is an integer from 1 to 10 and L is selected from the group consisting of:

(1)

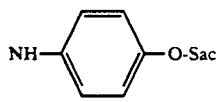

wherein Sac is a mono-, di- or trisaccharide;

(2)

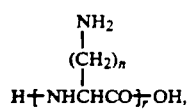

or a pharmaceutically acceptable cationic or anionic salt thereof, wherein n is three or four, r is an integer from 3 to 200 and the chroman is attached to L by the replacement of a hydrogen on a sidechain nitrogen; and (3) [—NH(CH$_2$)$_p$NH—]$_q$—D wherein p is an integer from 2 to 12, D is a functionalized dextran of molecular weight from about 1250 to about 3000, and g is an integer from 1 to 12, the value of which is not less than m and is in the range from about $1 \times 10^{-4}$ to about $7 \times 10^{-4}$ times the average molecular weight of D.

2. A compound according to claim 1 wherein L is [—NH(CH$_2$)$_p$NH-]$_q$—D.

3. A compound according to claim 2 wherein p is six.

4. A compound according to claim 3 wherein D is a dextran of average molecular weight from about 1250 to about 10,000, q is from 1 to 6 and m is from 1 to 5.

5. A compound according to claim 4 wherein D is a dextran of average molecular weight 9400, q is from 4 to 6 and m is 4 to 5.

6. A compound according to claim 1 wherein L is

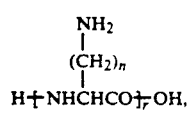

or a pharmaceutically acceptable cationic or anionic salt thereof.

7. A compound according to claim 6 wherein m is from 2 to 10 and n is 4.

8. A compound according to claim 7 wherein r is from about 65 to about 75 and m is 3 or 4.

9. A compound according to claim 7 wherein r is from about 140 to about 160 and m is from 2 to 4.

10. A compound according to claim 9 wherein m is 2 or 3.

11. A compound according to claim 1 wherein L is

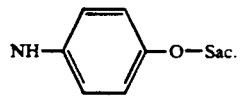

12. A compound according to claim 11 wherein Sac is a disaccharide.

13. A compound according to claim 12 wherein said disaccharide is lactose, cellobiose, gentiobiose or maltose.

14. A compound according to claim 13 wherein said disaccharide is lactose.

15. A compound according to claim 11 wherein Sac is a monosaccharide.

16. A compound according to claim 15 wherein said monosaccharide is galactose.

17. A compound of 6-hydroxy-2,5,7,8-tetramethylchroman-2-carboxylic acid and amine-derivatized dextran prepared by a process comprising the steps of:

(1) reacting dextran of average molecular weight about 9400 with about 0.5 equivalents of sodium periodate to produce an oxidized dextran;

(2) condensing said oxidized dextran at a concentration of 0.5% in aqueous buffer with about 10 equivalents of 1,6-hexanediamine at pH about 7.2 to produce a dextran-hexanediamin Schiff base;

(3) reducing said dextran-hexanediamine Schiff base with about 10 equivalents of sodium borohydride at pH about 9.0 to produce an aminohexylaminodextran; and (4) coupling said aminohexylaminodextran with about 1 equivalent of 6-hydroxy-2,5,7,8-tetramethylchroman-2- carboxylic acid in the presence of about 2 equivalents of 1-(3-dimethylamino)-3-ethylcarbodiimide at pH about 5.5 to about 6.5.

18. A method for protecting a cell from injury that is associated with reperfusion following ischemia, which method comprises providing said cell with an amount of a compound according to claim 1 effective to inhibit reperfusion injury.

19. A method for protecting a cell from injury that is associated with reperfusion following ischemia, which method comprises providing said cell with an amount of a compound according to claim 5 effective to inhibit reperfusion injury.

20. A method for protecting a cell from injury that is associated with reperfusion following ischemia, which method comprises providing said cell with an amount of a compound according to claim 10 effective to inhibit reperfusion injury.

21. A method for protecting a cell from injury that is associated with reperfusion following ischemia, which method comprises providing said cell with an amount of a compound according to claim 14 effective to inhibit reperfusion injury.

22. A method for protecting a cell from injury that is associated with reperfusion following ischemia, which method comprises providing said cell with an amount of a compound according to claim 15 effective to inhibit reperfusion injury.

23. A method for protecting a mammal from tissue injury that is associated with reperfusion following ischemia, which method comprises introducing into the blood circulation of said mammal, in an amount effective to inhibit reperfusion injury, a compound according to claim 1.

24. A method for protecting a mammal from tissue injury that is associated with reperfusion following ischemia, which method comprises introducing into the blood circulation of said mammal, in an amount effective to inhibit reperfusion injury, a compound according to claim 14.

25. A method for protecting a mammal from tissue injury that is associated with reperfusion following ischemia, which method comprises introducing into the blood circulation of said mammal, in an amount effective to inhibit reperfusion injury, a compound according to claim 15.

26. A composition for protecting a mammal from tissue injury associated with reperfusion after ischemia, said composition comprising an amount of a compound according to claim 1 in a pharmaceutically acceptable vehicle.

27. A composition for protecting a mammal from tissue injury associated with reperfusion after ischemia, said composition comprising an amount of a compound according to claim 14 in a pharmaceutically acceptable vehicle.

28. A composition for protecting a mammal from tissue injury associated with reperfusion after ischemia, said composition comprising an amount of a compound according to claim 15 in a pharmaceutically acceptable vehicle.

* * * * *

UNITED STATES PATENT AND TRADEMARK OFFICE
CERTIFICATE OF CORRECTION

PATENT NO.  : 5,099,012

DATED       : March 24, 1992

INVENTOR(S) : Donald A.G. Mickle and Tai-Wing Wu

It is certified that error appears in the above-identified patent and that said Letters Patent is hereby corrected as shown below:

Column 2, line 28: "12, L the" should read -- 12, the --.

Column 3, line 14: "6hydroxy" should read -- 6-hydroxy --.

Column 4, line 12: "e,ovs/M/w" should read -- $\bar{M}w$ --.

Column 4, line 43: "e,ovs/M/w" should read -- $\bar{M}w$ --.

Column 7, line 9: "e,ovs/M/w" should read -- $\bar{M}w$ --.

Column 8, line 32: "unlysec" should read -- unlysed --.

Column 11, line 21: "[q" should read -- ]q --.

Column 11, line 23: "3000" should read -- 30000 --.

Column 11, line 24: "g" should read -- q --.

Signed and Sealed this

Nineteenth Day of October, 1993

Attest:

BRUCE LEHMAN

Attesting Officer

Commissioner of Patents and Trademarks